(12) United States Patent
Aiken et al.

(10) Patent No.: US 7,169,290 B1
(45) Date of Patent: Jan. 30, 2007

(54) BIOSENSOR FOR METAL ANALYSIS AND SPECIATION

(75) Inventors: Abigail M. Aiken, Pullman, WA (US); Brent M. Peyton, Pullman, WA (US); William A. Apel, Idaho Falls, ID (US); James N. Petersen, Moscow, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 10/937,220

(22) Filed: Sep. 8, 2004

Related U.S. Application Data (62) Division of application No. 10/189,035, filed on Jul. 2, 2002, now Pat. No. 6,811,997.

(51) Int. Cl.
*C12Q 1/00* (2006.01)

(52) U.S. Cl. .......................... 205/777.5; 435/9; 435/25

(58) Field of Classification Search ................. 435/25, 435/9; 205/777.5
See application file for complete search history.

(56) References Cited

U.S. PATENT DOCUMENTS

| | | | |
|---|---|---|---|
| 4,626,416 A | 12/1986 | DeVoe et al. | |
| 5,062,956 A | 11/1991 | Lupton et al. | |
| 5,149,656 A | 9/1992 | Bitton et al. | |
| 5,155,042 A | 10/1992 | Lupton et al. | |
| 5,217,594 A * | 6/1993 | Henkens et al. | 204/403.04 |
| 5,380,649 A | 1/1995 | Berry et al. | |
| 5,500,351 A * | 3/1996 | Eccles et al. | 205/777.5 |
| 5,501,958 A | 3/1996 | Berry et al. | |
| 5,597,702 A * | 1/1997 | Wong et al. | 435/18 |
| 5,672,470 A | 9/1997 | Hengstenberg et al. | |
| 5,681,739 A | 10/1997 | Turick et al. | |
| 5,786,162 A * | 7/1998 | Corbisier et al. | 435/7.32 |
| 5,942,103 A | 8/1999 | Wang et al. | |
| 6,068,971 A | 5/2000 | Berry et al. | |
| 6,383,388 B1 | 5/2002 | Krauter et al. | |
| 6,706,474 B1 | 3/2004 | Lu et al. | |
| 6,811,997 B2 * | 11/2004 | Aiken et al. | 435/25 |
| 2002/0090738 A1 * | 7/2002 | Cozzette et al. | 436/518 |
| 2002/0127623 A1 * | 9/2002 | Minshull et al. | 435/7.92 |
| 2003/0136673 A1 * | 7/2003 | Pilloud et al. | 204/403.1 |
| 2004/0224868 A1 * | 11/2004 | Meyerhoff et al. | 510/320 |

OTHER PUBLICATIONS

Gilliam, Mary B., et al., A Spectrophotometric Assay for Nitrate Using NADPH Oxidation by *Aspergillus* Nitrate Reductase, *Analytical Biochem.*, vol. 212, pp. 359-365, Feb. 19, 1993.

Kneer, Ralf, et al., Phytochelatins Protect Plant Enzymes for Heavy Metal Poisoning, *Photochemistry*, vol. 31, No. 8, pp. 2663-2667, Nov. 18, 1991.

Krawczynski vel Krawczyk, Tadeusz, Analytical Applications of Inhibition of Enzymatic Reactions, *Chem. Anal.* (Warsaw), vol. 43, pp. 135-158, 1998.

Sharma, Shanti S., et al., In Vitro Alleviation of Heavy Metal-Induced Enzyme Inhibition by Proline, *Photochemistry*, vol. 49, No. 6, pp. 1531-1535, Mar. 1998.

\* cited by examiner

*Primary Examiner*—Ralph Gitomer
(74) *Attorney, Agent, or Firm*—TraskBritt, PC (57) ABSTRACT

A biosensor for metal analysis and speciation is disclosed. The biosensor comprises an electron carrier immobilized to a surface of an electrode and a layer of an immobilized enzyme adjacent to the electrode. The immobilized enzyme comprises an enzyme having biological activity inhibited by a metal to be detected by the biosensor.

20 Claims, 11 Drawing Sheets

BIOSENSOR FOR METAL ANALYSIS AND SPECIATION

RELATED APPLICATIONS

The present application is a divisional of U.S. patent application Ser. No. 10/189,035, filed on Jul. 2, 2002, now U.S. Pat. No. 6,811,997, issued Nov. 2, 2004.

GOVERNMENT RIGHTS

The United States Government has rights in the following invention pursuant to Contract No. DE-AC07-99ID13727 between the United States Department of Energy and Bechtel BWXT Idaho, LLC and pursuant to National Science Foundation Contract No. 9972817.

BACKGROUND OF THE INVENTION

1. Field of the Invention

A method of detecting a metal in a sample is disclosed. More specifically, a method of detecting chromium in an aqueous sample is disclosed.

2. State of the Art

Metals are a significant component of environmental pollutants and contaminants in soil and water. Metals are present at numerous locations around the world, largely from their use in a variety of commercial processes. One of these metals, chromium, is the second most common inorganic contaminant in hazardous waste sites in the Unites States, behind only nitrate. Chromium contaminants are typically present in hazardous waste sites in a trivalent form, Cr(III), and a hexavalent form, Cr(VI), also referred to herein as $Cr^{3+}$ and $Cr^{6+}$, respectively. Cr(VI), the more soluble of the two species, is known to be toxic to humans, animals, and plants. On the other hand, Cr(III) is an essential nutrient and one of the best selling dietary supplements in the United States.

The presence of chromium in environmental samples is typically detected by inductively coupled plasma atomic electron spectrometry ("ICP/AES"), inductively couple plasma mass spectrometry ("ICP/MS"), atomic absorption spectroscopy ("AAS"), or wet chemical methods. These techniques have detection limits ranging from parts per trillion to parts per billion. While these techniques are relatively accurate, they are time intensive and require expensive equipment. The current standard analytical technique for total chromium, which includes Cr(VI) and Cr(III), is inductively coupled argon plasma mass spectrometry ("ICP/MS"), which requires expensive capital investment (approximately $200,000) with additional per sample costs in the range of $30–$100. In addition, the equipment is typically massive, immobile and is not suited for use in field testing.

While current techniques detect total chromium, there is no direct, inexpensive method of distinguishing between the Cr(III) and Cr(VI) valence states of chromium. In addition, no direct method of quantitatively measuring Cr(III) exists. One technique for differentiating between Cr(VI) and Cr(III) requires that the samples first be separated by ion-exchange techniques, followed by analysis with AAS or ICP techniques to individually determine the concentrations of Cr(VI) and Cr(III). A second technique uses a colorimetric assay to determine the Cr(VI) concentration. The total chromium is then determined by either AAS or ICP techniques. Then, the Cr(III) concentration is calculated as the difference between total chromium and Cr(VI). However, this method may be inaccurate as it assumes that no other forms of chromium exist in the sample.

Biochemical means of analyzing soil and water samples, such as enzymatic methods, have recently received increased attention. Enzymatic assays are able to detect metals or pesticide inhibitors of the enzyme with greater speed and economy than traditional analytical techniques due to the lower equipment cost, compact size, portability and rapid test times of the enzymatic biosensors. These assays utilize the inhibitory effects that specific metal ions have on the activity of specific enzymes. For example, the enzymatic activities of urease, glucose oxidase, peroxidase, acetyl- or butyryl-cholinesterase, oxalate oxidase, alkaline phosphatase, xanthine oxidase, isocitric or lactate dehydrogenase, and B-fructofuranosidase are inhibited by mercury ("Hg"), copper ("Cu"), silver ("Ag"), cadmium ("Cd"), lead ("Pb"), cobalt ("Co"), manganese ("Mn"), zinc ("Zn"), bismuth ("Bi"), beryllium ("Be"), nickel ("Ni"), Cr(III), and/or Cr(VI). Tadeusz Krawczynski vel Krawczyk, *Chem. Anal. (Warsaw)* 43, 135 (1998).

Some of these metals, such as chromium, cadmium, copper, lead, and zinc, are known to substantially inhibit the enzymatic activity of nitrate reductase ("NR"). Even small amounts of these metals and pesticides are known to inhibit NR. NR is an enzyme that catalyzes the conversion of nitrate ("$NO_3^-$") to nitrite ("$NO_2^-$"). NR is produced by a variety of animals, plants, and microorganisms, including fungi. For instance, *Aspergillus niger* produces a nicotinamide adenine dinucleotide ("NADH") or nicotinamide adenine dinucleotide phosphate ("NADPH") bispecific form of assimilatory NR (EC 1.6.6.2) that catalyzes the reduction of $NO_3^-$ to $NO_2^-$. NR is a homodimer composed of two identical subunits of approximately 100 kDa, each of which contains three cofactors, flavin adenine dinucleotide ("FAD"), heme-iron (heme-Fe) and Mo-molybdopetrin (Mo-MPT) in a 1:1:1 ratio. All known sequences of NR have been found to contain one conserved cysteine ("Cys") residue that is located in a cytochrome b fragment of the enzyme. Site-directed mutagenesis of the cytochrome b domain of corn leaf NADH:NR showed that this Cys residue is not essential for NADH binding or NADH:NR activity, but is essential for highly efficient catalytic transfer of electrons from the NAD(P)H to FAD. It has also been determined that there are other key Cys residues present in most NR enzymes that are involved in binding the molybdopetrin as well as joining the enzymes subunits. The presence of multiple Cys in NR lends it to be highly sensitive to inhibition by metals because many of these metals, such as Cu and Pb, have high binding affinities for the thiol groups that are present in the Cys side chains.

In evaluating known or suspected sites of metal contamination or while conducting routine drinking water analyses, hundreds of samples may be taken for analysis, many of which may not be contaminated. Thus, it would be desirable to measure Cr(III) by a less expensive method than those currently available. In addition, it would be desirable to speciate Cr(VI) from Cr(III) using a simple, less expensive method than is offered by the current state of the art.

BRIEF SUMMARY OF THE INVENTION

A method of detecting a metal in a sample is disclosed. The method comprises providing the sample potentially comprising a metal. At least a portion of the sample is added to a reagent solution comprising an enzyme and a substrate, where the enzyme is of a type inhibited by the metal. An enzymatic activity in the sample is measured and compared to an enzymatic activity in a control solution to determine the concentration of the metal present in the sample.

In one embodiment, the metal to be detected is chromium. Chromium is detected using a reagent solution comprising nitrate reductase, NADPH, and nitrate. The nitrate reductase converts the nitrate to nitrite, which may be detected colorimetrically.

A method of detecting a metal in a sample comprising a plurality of metals is also disclosed. The method comprises adding a chelating agent to a portion of the sample. The first chelating agent chelates a portion of the metals without chelating the metal to be detected. Another chelating agent is added to the portion of the sample to chelate another portion of the metals without chelating the metal to be detected. When only the metal to be detected remains unchelated, a reagent solution comprising an enzyme and a substrate is added to the portion of the sample. The metal to be detected inhibits the enzyme and is easily detected. The method also comprises quantifying the concentration of the metal in the sample.

A method of detecting a valence state of a metal in a sample is disclosed. The method comprises providing a sample comprising a metal, wherein the metal is present in a plurality of valence states. At least one chelating agent is added to a portion of the sample to chelate at least one portion of the valence states without chelating a valence state of interest. Additional chelating agents are added to the portion of the sample to chelate additional portions of the valence state without chelating the valence state of interest. When the valence state of interest is the only unchelated valence state remaining in the sample, a reagent solution comprising an enzyme and a substrate is added to the portion of the sample, wherein the enzyme is inhibited by the valence states of the metal. The valence state of interest of the metal is then detected and its concentration in the sample is determined.

A method of detecting a valence state of a metal in a sample is also disclosed. The method comprises providing a sample comprising a plurality of metals, wherein at least one metal is present in a plurality of valence states. A chelating agent is added to a portion of the sample to chelate the plurality of metals without chelating the at least one metal present in a plurality of valence states. The plurality of valence states of the at least one metal present in the portion of the sample are separated by chromatographic techniques to isolate a valence state of interest. Then, a reagent solution comprising an enzyme and a substrate is added to the portion of the sample. The enzyme is inhibited by the plurality of valence states of the metal. The valence state of interest of the metal is then detected and quantified.

BRIEF DESCRIPTION OF THE SEVERAL VIEWS OF THE DRAWINGS

In the drawings, which illustrate what is currently considered to be the best mode for carrying out the invention.

DETAILED DESCRIPTION OF THE INVENTION

A method of detecting a metal in a sample is disclosed. The method comprises providing the sample potentially comprising a metal. At least a portion of the sample is added to a reagent solution comprising an enzyme and a substrate, where the enzyme is of a type inhibited by the metal. An enzymatic activity in the sample is measured and compared to an enzymatic activity in a control solution to determine whether the metal is present in the sample. A concentration of the metal in the sample may also be determined or quantified. A method of detecting a valence state of the metal and determining the concentration of the valence state present in the sample is also disclosed.

In one embodiment, the metal to be detected is chromium. Chromium is detected using a reagent solution comprising nitrate reductase, NADPH, and nitrate. The nitrate reductase converts the nitrate to nitrite, which is detected colorimetrically. The chromium in the sample modifies the enzyme activity, allowing the chromium concentration to be determined.

A method of detecting a metal in a sample comprising a plurality of metals is also disclosed. The method comprises adding a chelating agent to a portion of the sample. The chelating agent chelates a portion of the metals without chelating the metal to be detected. Another chelating agent is added to the portion of the sample to chelate another portion of the metals without chelating the metal to be detected. When only the metal to be detected remains, a reagent solution comprising an enzyme and a substrate is added to the portion of the sample. The remaining metal inhibits the enzyme and is detected. A concentration of the metal is also determined or quantified.

A method of detecting a valence state of a metal in a sample is disclosed. The method comprises providing a sample comprising a metal, wherein the metal is present in a plurality of valence states. At least one chelating agent is added to a portion of the sample to chelate at least one portion of the valence states without chelating a valence state of interest. When only the valence state of interest remains unchelated in the sample, a reagent solution comprising an enzyme and a substrate is added to the portion of the sample. The enzyme that is used in the reagent solution is inhibited by substantially all of the plurality of valence states of the metal. The valence state of interest is then detected and its concentration in the sample quantified by measuring the enzymatic activity in the sample.

A method of detecting a valence state of a metal in a sample using chromatographic techniques is also disclosed. The method comprises providing a sample comprising a plurality of metals, wherein at least one metal of the plurality of metals is present in a plurality of valence states. A chelating agent is added to at least a portion of the sample to chelate the plurality of metals without chelating the metal present in a plurality of valence states. The valence states of the metal present are separated to isolate a valence state of interest. Then, a reagent solution comprising an enzyme and a substrate is added to the portion of the sample. The enzyme is inhibited by the plurality of valence states of the metal. The valence state of interest of the metal is then detected and quantified.

In the method of the present invention, the metal to be detected may be any metal. The metal to be detected may include, but is not limited to, transition metals such as chromium ("Cr"), copper ("Cu"), cadmium ("Cd"), nickel ("Ni"), zinc ("Zn"), arsenic ("As"), mercury ("Hg"), or silver ("Ag"). The metal to be detected may also include non-transition metals, such as lead ("Pb"). The sample may be a water sample, a soil sample, or any other sample of material believed to be contaminated or polluted with at least one metal to be detected and quantified.

The method comprises providing a reagent solution comprising an enzyme and a substrate. The enzyme may be selected based on the metal to be detected and the desired sensitivity of the assay. The enzyme catalyzes a known reaction from a substrate to a product, where production of the product or reaction of the substrate is susceptible to being determined colorimetrically. The activity of the enzyme may be inhibited by the metal to be detected. In addition, the enzyme may be sensitive to the inhibitor over an environmentally significant concentration range. While the examples below describe a method of detecting Cr using NR as the enzyme, other enzymes may be used to detect other metals, provided that the metal to be detected is an inhibitor of the enzyme. It is also contemplated that more than one enzyme may be used in the reagent solution to detect the metal.

As used herein, the term "substrate" refers to a substance that is acted on by the enzyme. The substrate in the reagent solution may be selected based on the enzyme that is used. The substrate and enzyme have an affinity for each other such that the enzyme converts the substrate to the product. Since the conversion of the substrate to the product may be determined colorimetrically, the determination of enzymatic activity is fast and relatively simple.

The reagent solution comprising the enzyme and substrate may be added to the sample or to a portion of the sample. An enzymatic activity in the sample may be determined by monitoring the reaction of the substrate to the product as known in the art, such as by using a calorimetric assay. The enzymatic activity in the calorimetric assay may be easily determined using a visible light spectrophotometer or multi-well plate spectrophotometer. To determine whether the metal is present in the sample, the enzymatic activity of the sample may be compared to an enzymatic activity of a control solution, which comprises the enzyme and the substrate. In other words, the control solution does not comprise the metal to be detected. If the metal is present in the sample, the enzymatic activity of the sample is decreased relative to the enzymatic activity of the control solution. However, if the metal is not present in the sample, the enzymatic activity of the sample is substantially similar to the enzymatic activity of the control sample.

In addition to detecting the metal, the enzymatic method may be used to determine the concentration of, or quantify, the metal. A signal generated by the visible light spectrophotometer is proportional to the degree to which the metal inhibits the enzyme. Since the extent of inhibition is also dependent on the concentration of the metal in the sample, the signal that is generated by the visible light spectrophotometer is a direct function of the concentration of the metal in the sample. The concentration of metal may be quantified by comparing the detected enzymatic activity to a standard curve, as known in the art.

The method previously described may be used to detect and quantify the metal of interest in a relatively clean sample. However, typical samples are not always clean and it may be necessary to detect and quantify the metal of interest in a sample comprising a plurality of metals. In addition, it may be necessary to detect and quantify a particular valence state of the metal of interest in a sample where the metal is present in a plurality of valence states.

The method may be used to detect and quantify a metal of interest by chelating additional metals from the sample. These additional metals inhibit the enzyme and may interfere with detecting the enzymatic activity of the metal of interest. The inhibitory effects of the additional metals may be eliminated by adding an array or matrix of chelating agents to the sample to chelate the additional metals, thereby making the additional metals unavailable to inhibit the enzyme. The array of chelating agents may remove the inhibitory effects of the additional metals without interfering with the inhibitory effects of the metal of interest. Since the effects of the additional metals are eliminated, the metal of interest may be easily detected and quantified. Any number of chelating agents may be used in the array as long as the chelating agents do not affect the inhibitory effects of the metal of interest. While the examples disclosed herein use one or two chelating agents, it is understood that any number of chelating agents may be used to chelate the undesired metals.

The array of chelating agents may comprise a plurality of chelating agents, including but not limited to, ethylenediaminetetraacetic acid ("EDTA"), nitrilotriacetic acid ("NTA"), and citrate. In addition, ion exchange resins, biological agents such as siderophores, or enzymes that have a high affinity for a particular metal may be used as the chelating agent. Each of the chelating agents may chelate a portion of the metals in the sample so that ultimately only the metal of interest remains unchelated and has a measurable, inhibitory effect on the enzyme. For instance, a first chelating agent may chelate a first portion of the metals in the sample without chelating the metal of interest. If the metal of interest is the only metal remaining in the sample that has an inhibitory effect on the enzyme, the metal of interest may be detected as previously described. However, if additional metals remain, a second chelating agent may be used to chelate a second portion of the remaining metals without chelating the metal of interest. Once all the metals except the metal of interest have been chelated, the metal of interest may be detected and quantified as previously described. It is also contemplated that the array of chelating agents may be used to detect more than one metal of interest.

The array of chelating agents may also be used to detect a valence state of the metal of interest in a sample where the metal of interest is present in multiple valence states. For instance, a first chelating agent may be used to eliminate the inhibitory effects of a portion of the metals without affecting any of the valence states of the metal of interest. A second chelating agent may be used to eliminate the inhibitory effects of one or more of the valence states of the metal of interest without affecting the inhibitory effects of a valence state of interest. Since the activity of the valence state of interest is unaffected by the array of chelating agents, the valence state of interest may be easily detected and quantified, as previously described. It is understood that the array of chelating agents may be chosen so that the metal of interest or valence state of interest is not chelated while the chelating agents selectively chelate the metals and valence states that are not of interest.

It is also contemplated that the first chelating agent may be used to eliminate the inhibitory effects of a first portion of the metals without affecting any of the valence states of the metal of interest. The second chelating agent may be used to eliminate the inhibitory effects of a second portion of the metals without affecting any of the valence states of the metal of interest. Additional chelating agents may be used to eliminate the inhibitory effects of the valence states until only the valence state of interest is remaining. This valence state may then be easily detected and quantified as previously described.

It is also contemplated that a separation step may be used to separate the valence states of the metal of interest after the inhibitory effects of the metals that are not of interest have been eliminated. The metal of interest may be present in multiple valence states, with each valence state having a different charge. For example, one species of the metal of interest may be noncharged or cationic while the other species of the metal of interest may be a divalent anion. The valence states may be separated based upon this charge difference using chromatographic techniques, such as ion exchange chromatography. Depending on the charges of the different valence states, the valence states of the metal of interest may be separated using anion or cation exchange chromatography. The valence states may be separated by adding a small amount of an ion exchange resin to scavenge one of the species, thereby leaving the other species, the valence state of interest, to inhibit the enzymatic activity in the sample. The valence state of interest may then be detected and quantified, as previously described.

Figure 13A:
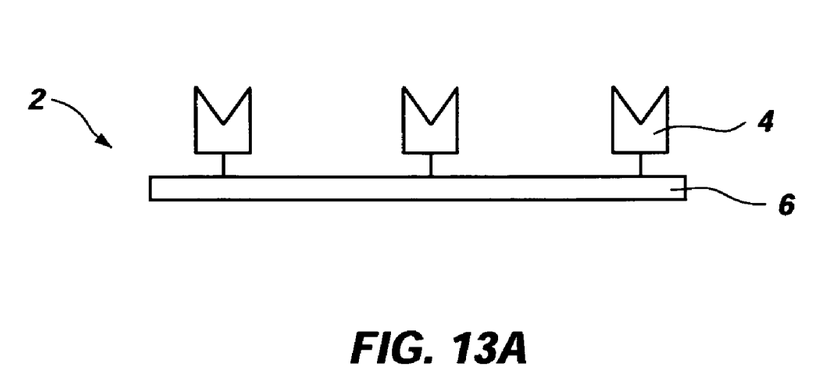
FIGS. 13A and 13B are schematic representations of a biosensor according to the present invention.
Figure 13B:
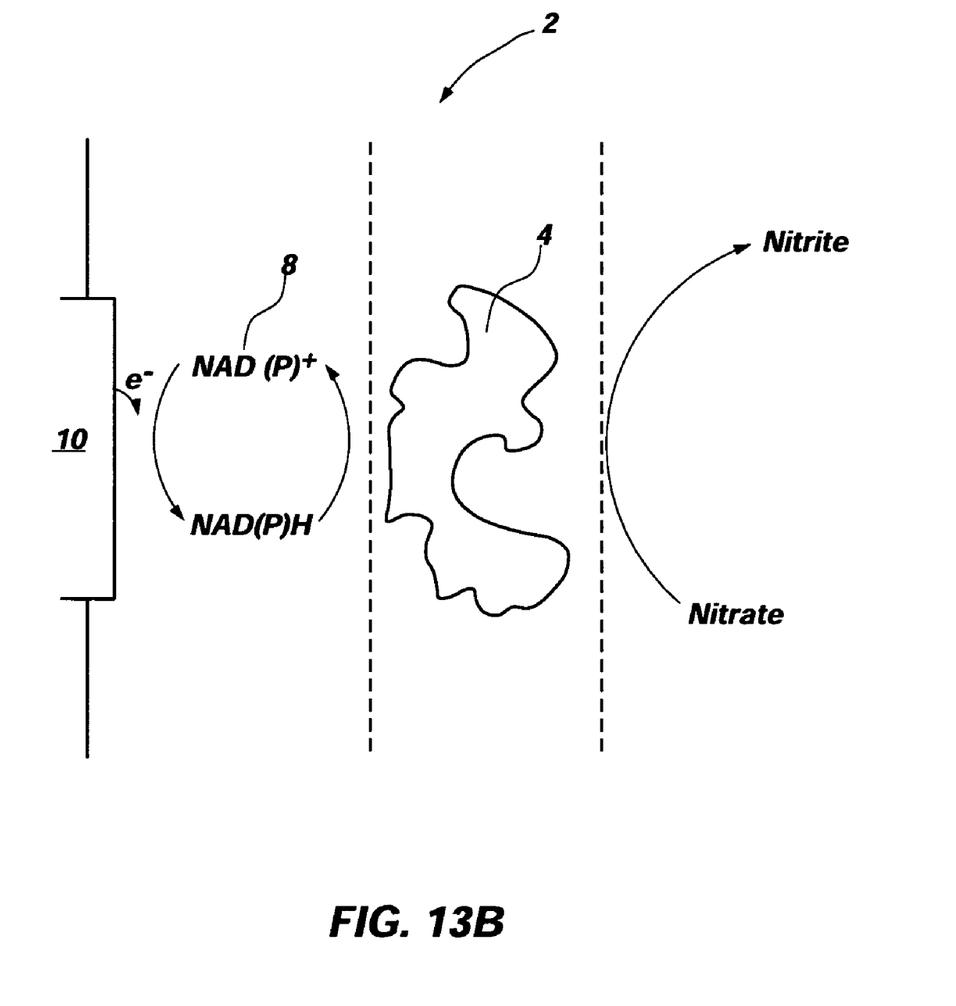

A biosensor 2 for detecting metals in numerous samples may be fabricated to use the methods described herein. The biosensor 2 may comprise the enzyme 4 immobilized on a probe 6, as shown in FIG. 13A. The probe 6 may include a solid support known in the art, such as a waveguide, beads, a 96-well plate, a film, or a chip. In addition, amperometric biosensor designs are commonly used with reduction/oxidation ("redox") enzymes 4, such as NR. These biosensors utilize the production of electrons, which occurs during the oxidation or reduction of the substrate, to generate a signal. A multilayer biosensor 2 may be used where an electron carrier 8, such as NAD(P), is covalently immobilized to a surface of an electrode 10. The redox enzyme 4, which may be NR, is crosslinked to a first layer of the biosensor 2, as shown in FIG. 13B. The electron carrier 8 is covalently attached to a gold electrode 10 to form the first layer and the NR 4 is crosslinked to this layer with glutaraldehyde. An electric potential is applied to the electrode 10, which allows the electroreduction of $NAD(P)^+$ to $NAD(P)H$. This in turn leads to the reduction of the nitrate to nitrite as catalyzed by NR, which generates a measurable current proportional to the nitrate concentration. The presence of a metal that has an inhibitory effect on the enzymatic activity decreases the current generated at a given nitrate concentration. This decrease in current is proportional to the concentration of the metal and, as a result, may be used to both detect and quantify the metal. Furthermore, since the biosensor 2 is preferably used in repeated measurements of metal concentrations, the enzyme 4 may be reused by adding a chelating agent to restore enzymatic activity to previously inactivated enzyme.

The methods previously described may be used in a laboratory or in the field as a sensitive and cost effective technique to detect and quantify metals. In addition to measuring enzymatic activity with a visible light spectrophotometer, the enzymatic activity may be measured with a multi-well spectrophotometer. Multi-well plates may be preloaded with the proper amount of the reagents used in the assay to allow rapid, simultaneous analyses of numerous samples.

The methods previously described may be used to quantify metals in water and soil samples. The methods may be used in large scale routine screening of drinking water samples or industrial process streams in which the majority of the contents of the samples are known. Considering the high cost and time spent processing multiple samples using traditional techniques such as ICP/MS and AAS, the need for a rapid initial screening process is apparent. The detection of various metals by enzymatic inhibition has the potential to initially screen a large volume of samples for contamination. Contaminated samples identified by the enzymatic inhibition method may pinpoint areas that need the sensitivity and accuracy that can be attained using ICP/MS and AAS analysis. Screening large numbers of samples via enzymatic inhibition will not only reduce testing time, but will also decrease overall costs because fewer samples will need to be tested using traditional analytical techniques.

The exemplary methods described herein may be used to detect and quantify Cr in a relatively clean sample. To detect Cr, a reagent solution comprising NR, NADPH, and a nitrate ("$NO_3^-$") compound is provided. The nitrate may be potassium nitrate or any other water-soluble form of nitrate. NR is known to catalyze the reaction of nitrate to nitrite ("$NO_2^-$"). The production of nitrite is detected colorimetrically by monitoring the derivatization of the nitrite, as described in R. Kneer et al., *Phytochemistry*, 31:2663–2667 (1992), or the consumption of NADPH, the electron donor in the reduction of nitrate to nitrite, as described in Gilliam et al., *Anal. Biochem.*, 212:359–365 (1993). The enzymatically catalyzed reaction of nitrate to nitrite is known to be inhibited by Cr, and, more specifically, Cr(III) and Cr(VI). Since NR is sensitive to Cr(III), it is possible to detect and quantify Cr(III) in clean, aqueous samples.

The reagent solution comprising NR, NADPH, and the nitrate compound is added to the sample or to a portion of the sample. The NR activity in the sample is determined by monitoring the production of nitrite. To determine whether Cr is present in the sample, the NR activity is compared to the enzymatic activity of a control solution, which comprises the NR and the nitrate. If Cr is present in the sample, the NR activity of the sample is decreased relative to the enzymatic activity of the control solution. However, if Cr is not present in the sample, the NR activity of the sample is substantially similar to the enzymatic activity of the control sample. The concentration of Cr in the sample is quantified by comparing the detected enzymatic activity to a standard curve.

The methods described herein may also be used to detect Cr in the presence of other metals, such as Cd, Cu, Pb, and Zn, which are known to inhibit NR. The effects of the other metals are eliminated by adding a chelating agent, such as NTA, to the reagent solution. NTA chelates the Cd, Cu, Pb, and Zn and eliminates their inhibitory effects on NR without affecting either Cr(III) or Cr(VI), thereby allowing Cr to be detected and quantified in the sample.

The method may also be used to quantitatively differentiate or speciate between Cr(III) and Cr(VI) in a sample comprising both species of Cr. By adding EDTA to the sample, the inhibitory effects of Cr(III) are eliminated without affecting the inhibitory effect of Cr(VI). In samples comprising Cr(III), Cr(VI), and other metals, the effects of the other metals may be eliminated using NTA. Then, EDTA may be used to speciate between the Cr(III) and Cr(VI).

It is also contemplated that an anion exchange resin may be used to separate Cr(III) and Cr(VI) after the array of chelating agents has eliminated the inhibitory effects of metals that are not of interest. Species of Cr(VI) typically occur as chromate ($CrO_4^{2-}$) and dichromate ($Cr_2O_7^{2-}$), which are both divalent anions. In contrast, Cr(III) is cationic and, therefore, will not be exchanged when using an anionic exchange resin. Cr(III) and Cr(VI) may be separated by adding a small amount of anion exchange resin to scavenge the anionic Cr(VI) species, leaving only the Cr(III) to inhibit the NR activity. The concentration of Cr(III) may then be quantified.

The presence of Cr in samples may be measured in a lab or in the field with a multi-well spectrophotometer. The multi-well plates are preloaded with the proper amount of the reagents used in the assay, such as NR, $KNO_3$, NADPH, NTA, or EDTA, and the anion exchange resin, to allow the simultaneous, rapid analyses of multiple Cr(III) samples. This assay provides a rapid, inexpensive assay for detecting and quantifying Cr. Since the assay only requires the purchase of a visible light spectrophotometer, which costs approximately $500–$8000, and additional per sample costs of approximately $1–2, detecting Cr(III) by this method is significantly cheaper than the ICP-MS techniques used for most routine applications.

EXAMPLES

To determine the extent to which NR was sensitive to metals in aqueous samples, the activity of purified *A. niger* NR was evaluated in the presence of $Cd^{2+}$, $Cu^{2+}$, $Cr^{3+}$, $Cr^{6+}$, $Ni^{2+}$, $Pb^{2+}$, and $Zn^{2+}$ ions at concentrations ranging from 0.01 to 1000 µM. To determine a selective method of metal detection in aqueous samples, the ability of EDTA and NTA to form metal complexes and thus prevent NR inhibition by metals was also investigated. As many biosensors make use of an immobilized enzyme on a probe, the ability to reuse NR in repeated measurements of metal concentrations was investigated by using EDTA additions as a means of restoring enzymatic activity to previously inactivated NR.

All chemicals used in the assay were prepared using ultrapure water having a resistance of 18 MΩ or greater that was stored in HCl acid washed glassware. The buffers used in metal inhibition tests were 4-2-hydroxyethly-1-piperazine ethansulfonic acid ("HEPES"), 3-[N-morpholino]propane-sulfonic acid ("MOPS"), and piperazine-N,N'-bis[2-ethane sulfonic acid] ("PIPES"), which were obtained from Sigma-Aldrich Co. (St. Louis, Mo.). Potassium phosphate monobasic/potassium phosphate dibasic and tris[hydroxymethyl]aminomethane hydrochloride ("TRIS") were obtained from Fisher Scientific Company, LLC (Pittsburgh, Pa.). The pH of the TRIS, HEPES, MOPS and PIPES buffers was adjusted to 7.5 using either 3 M HCl or 1 M NaOH. The pH of the phosphate buffer was adjusted to 7.5 using a 100 mM solution of potassium phosphate monobasic.

Purified *A. niger* NR (E.C. 1.6.6.2) was obtained from Sigma-Aldrich Co. (St. Louis, Mo.) and was prepared fresh each day in a 0.35 mg ml$^{-1}$ stock solution (approximately 0.25 units ml$^{-1}$), which was buffered with 30 mM MOPS buffer at a pH of 7.5. Nicotinamide adenine dinulceotide phosphate ("NADPH"), which was also obtained from Sigma-Aldrich Co. (St. Louis, Mo.), was prepared fresh daily at a concentration of 0.35 mM in a 30 mM MOPS buffer at pH 7.5.

$KNO_3$ was obtained from Fisher Scientific Company, LLC (Pittsburgh, Pa.). The following metal salts were used to prepare metal stock solutions: $Cd_2Cl_4^-H_{10}O_5$, $CuCl_2^-2H_2O$, $CrCl_3^-6H_2O$, $NiCl_2^-6H_2O$, $PbCl_2$, $ZnCl_2$ and $K_2Cr_2O_7$. Stock solutions of NTA and EDTA, which were available from Sigma-Aldrich Co. (St. Louis, Mo.) and Fisher Scientific Company, LLC (Pittsburgh, Pa.), respectively, were prepared and adjusted to a pH of 7.5 using 1 N NaOH to adjust the NTA and 3 M HCl to adjust the EDTA.

Example 1

Measurement of NR Activity

NR activity was measured using the Griess reaction in which nitrite is colorimetrically determined by diazotization and diazomium coupling reactions of nitrite with sulfanilamide and N-(1-naphthyl)ethylenediamine. Measurements were conducted in 96-well microtiter plates, allowing multiple reactions to be quantified simultaneously. The assay followed the method as described in R. Kneer et al., *Phytochemistry*, 31:2663–2667 (1992), with modifications including the adaptation for use in a 96-well plate format, the reduction of the assay time to 5 minutes, and the substitution of a 12.5 mM MOPS buffer instead of the 33 mM TRIS buffer used.

The reaction was quenched with the addition of 40 µl of 1% (wt) sulfanilamide in 3 M HCl, which was shown to completely halt the enzymatic reduction of nitrate by substantially lowering the pH of the assay solution. This was followed by the addition of 40 µl 0.2% (wt.) N-(1-naphthyl) ethylenediamine. The absorbance of the resulting pink solution read at 540 nm was recorded after ten minutes using a microplate reader (HTS7000 Plus Bioassay Reader, Perkin Elmer, Conn.).

Negative controls containing all reagents except NR were run and analyzed for nitrite. An activity of 100% indicated the rate of nitrate conversion in the absence of Cr(III). Positive controls, which comprised no metal but comprised all other reagents, were also run. Additional controls comprising nitrite, NR and NADPH were run to rule out the possibility that NR reduced the nitrite.

NR activity is reported as a percentage of the experimentally measured activity of the positive (metal-free) control or as a ratio of the change in absorbance of a metal-containing sample to the change in absorbance of a positive (metal-free) control. An activity of 100% indicated the rate of nitrate conversion in the absence of the metal. Data points represent the averages of seven replicate experiments and error bars represent the standard deviation of those averages, unless otherwise stated.

Example 2

Evaluation of Buffer-Metal Interactions

To determine the buffer that would provide minimal metal-buffer complexation and, therefore, allow maximal metal inhibition to NR activity, an analysis of various pH buffers was performed. HEPES, MOPS, PIPES, phosphate, and TRIS buffers were individually evaluated in the presence of NR and 5 µM of each of the following metals: $Cr^{3+}$, $Cr^{6+}$, $Cd^{2+}$, $Cu^{2+}$, $Pb^{2+}$, and $Zn^{2+}$. An unbuffered assay system was used to establish a baseline of metal-induced enzyme inhibition. Reagents were added in the following order: the metal stock solution, the buffer solution, $KNO_3$ solution, NR, and NADPH.

For these buffer experiments, NR and NADPH solutions were prepared in water rather than in the 30 mM MOPS, as was done for all other experiments. The final concentration of all reagents was 30 mM of each respective buffer, 5 µM metal, 50 µg $ml^{-1}$ NR, 10 mM $KNO_3$ and 0.1 mM NADPH. NADPH addition initiated the reaction but NR activity was determined following the method described in Gilliam et al., *Anal. Biochem.*, 212:359–365 (1993), which is based on the rate of NADPH disappearance. The presence of NADPH, which has a peak absorbance at 340 nm, was monitored with respect to time for 3 minutes using a Hewlett Packard 8452A UV-Vis spectrophotometer. NR activity was then reported as a ratio of the change in absorbance of a metal-containing sample to the change in absorbance of a positive (metal-free) control. The inherent instability of NADPH and the potential for oxidation in the presence of the metals used in these experiments was accounted for in negative controls, which contained all reagents but NR.

Figure 1:
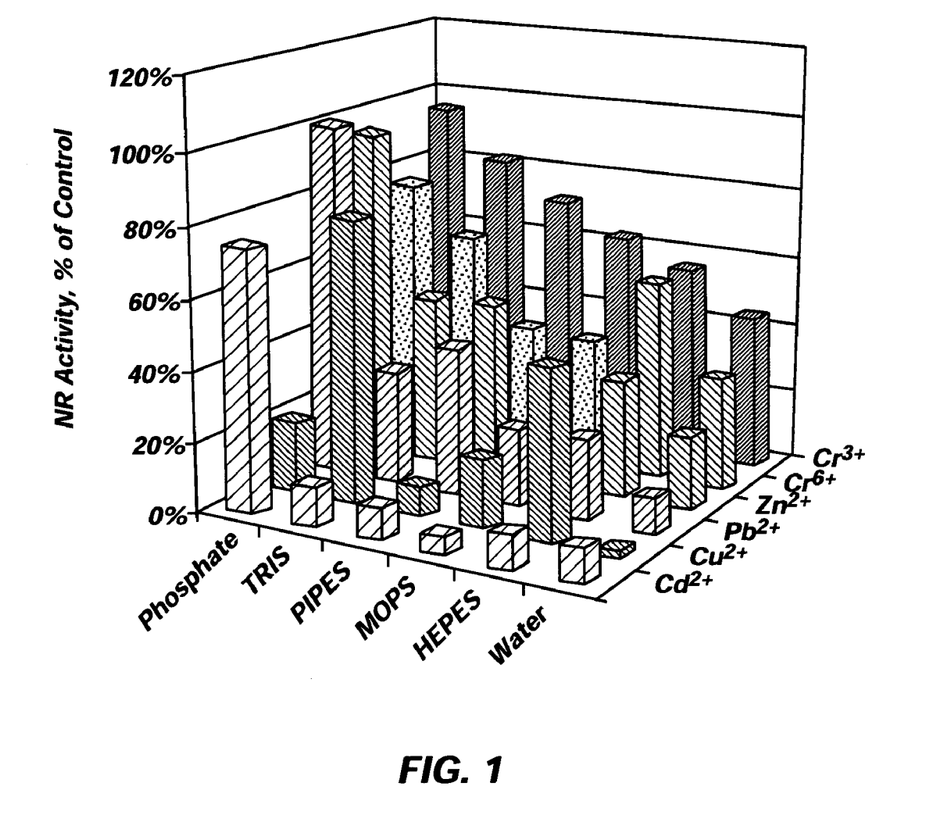
FIG. 1 shows the effect of various buffering systems on the extent of metal induced inhibition of NR.

To select a buffering system that allowed for maximum inhibition of the enzyme by metal ions, several common buffers, HEPES, MOPS, PIPES, Phosphate and TRIS were tested in metal inhibition assays. The buffers used in the assay affected the sensitivity of NR to the metal ions examined due to some of the buffers' ability to chelate metal ions, as shown in FIG. 1. NR activity is reported as the percent of a metal free control. Values represent the averages of five replicate experiments. NR activity assays were also run in an unbuffered water system to establish a baseline level of metal sensitivity and to determine if the buffers were shielding NR from inhibition by any of the metals that were examined. An unbuffered assay system was not selected for further experiments because the pH was not uniformly maintained for the various conditions under which NR activity would be measured. When compared to unbuffered water, the MOPS buffer did not preferentially bind the metals examined. Therefore, MOPS was chosen for use in subsequent metal inhibition assays over a wider range of metal concentrations. The phosphate and TRIS buffers appeared to selectively protect NR against different metals. In a phosphate buffered system, NR activity was inhibited by $Cu^{2+}$ ions while NR activity was relatively insensitive to $Cd^{2+}$, $Cr^{6+}$, $Pb^{2+}$ and $Zn^{2+}$. The opposite was found when the assay was conducted in a TRIS buffered system where NR was insensitive to $Cu^{2+}$ ions and was inhibited by $Cd^{2+}$, $Cr^{6+}$, $Pb^{2+}$, and $Zn^{2+}$.

Example 3

Measurement of Metal Inhibition

NR, NADPH, and $KNO_3$ were used in the same concentrations as in the metal-free NR and buffer evaluation assays. For metal-inhibition studies in the absence of a chelating agent, the appropriate concentration of metal stock solution was added to the NR and $KNO_3$ solution. The mixture was allowed to incubate at 25° C. for five minutes prior to the addition of NADPH to allow adequate time for the metal and NR to interact. A 12.5 mM MOPS buffer solution was used to maintain the pH at 7.5. Final metal concentrations in the assay solution ranged from 0.01 µM to 1000 µM. Enzyme activity was determined as described above by the calorimetric quantification of nitrite production and reported as a percentage of the nitrite produced in a metal-free control.

Figure 2:
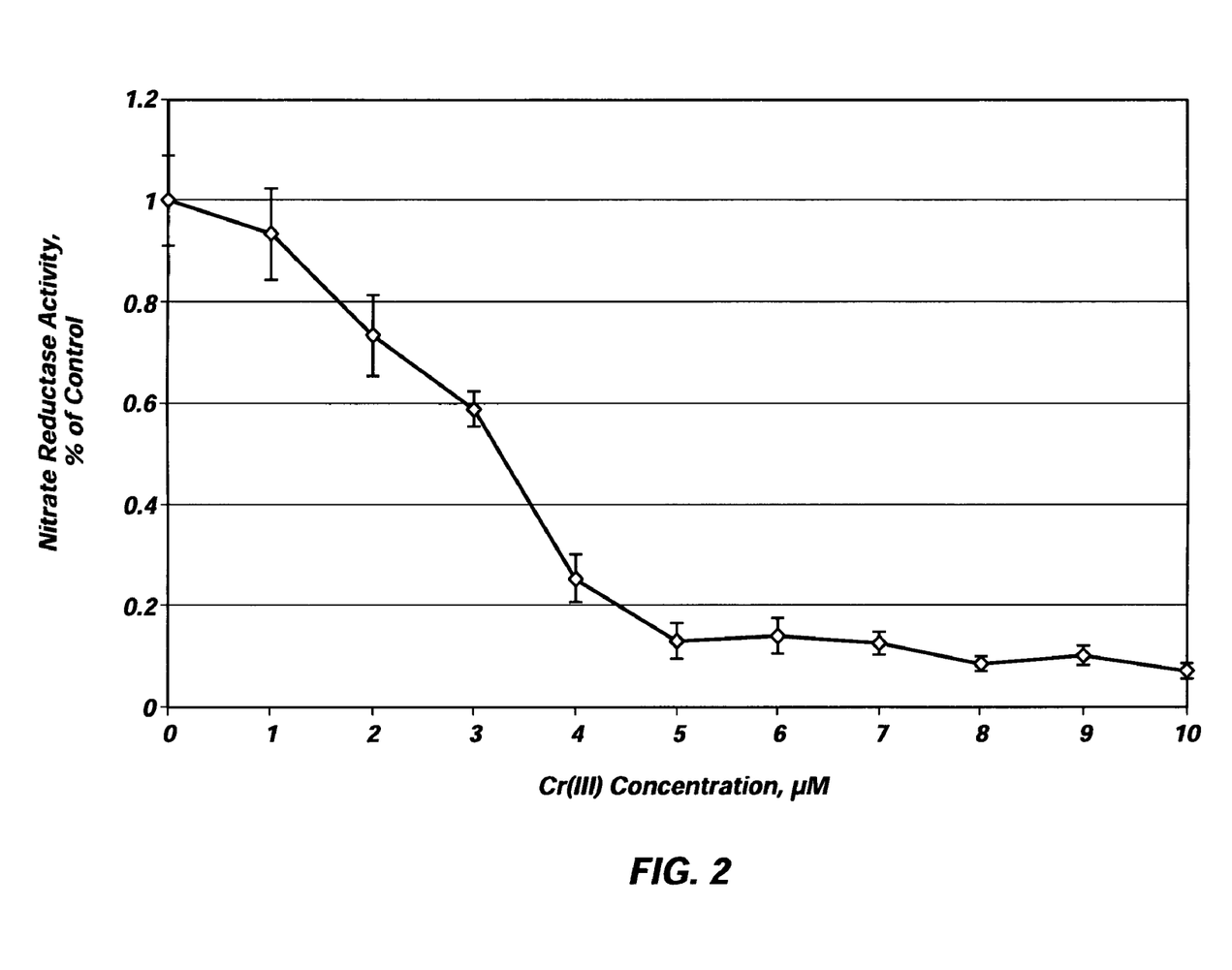
FIG. 2 is a graphic illustration of Cr(III) inhibition of NR at concentrations ranging from 0–10 µM.

The sensitivity of NR to Cr(III) was determined at concentrations ranging from 1 to 10 µM. As shown in FIG. 2, Cr(III) inhibited NR in this concentration range. To further determine the extent to which NR was sensitive to metals in aqueous samples, the activity of purified NR was evaluated in the presence of $Cd^{2+}$, $Cu^{2+}$, $Cr^{3+}$, $Cr^{6+}$, $Ni^{2+}$, $Pb^{2+}$, and $Zn^{2+}$ ions at concentrations ranging from 0.01 to 1000 µM. These experiments were run using a MOPS buffer, which showed the least overall affinity for the metals used in this study when compared to the other buffers.

Figure 3:
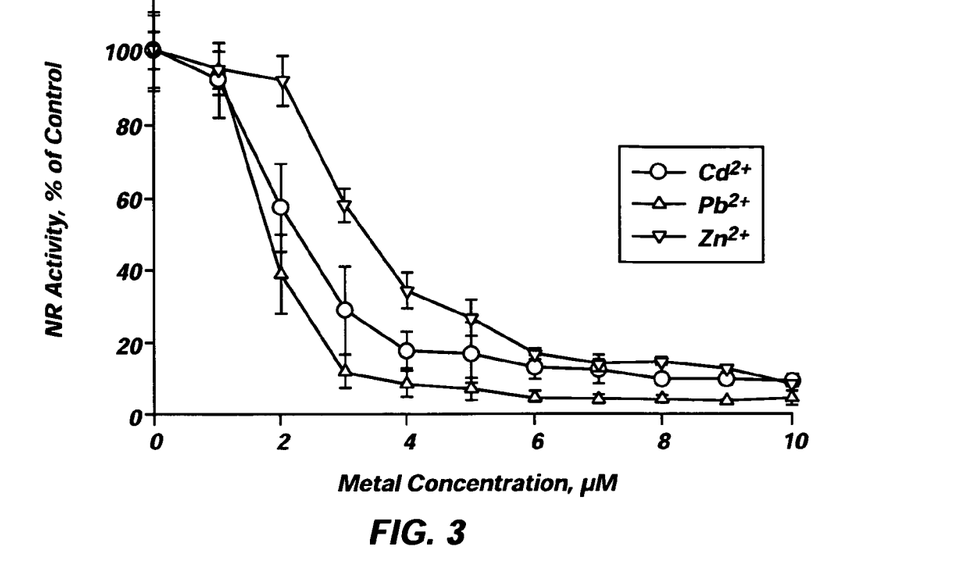
FIG. 3 is a graphic illustration of the impact of $Cd^{2+}$, $Pb^{2+}$ and $Zn^{2+}$ ions on NR activity.
Figure 4:
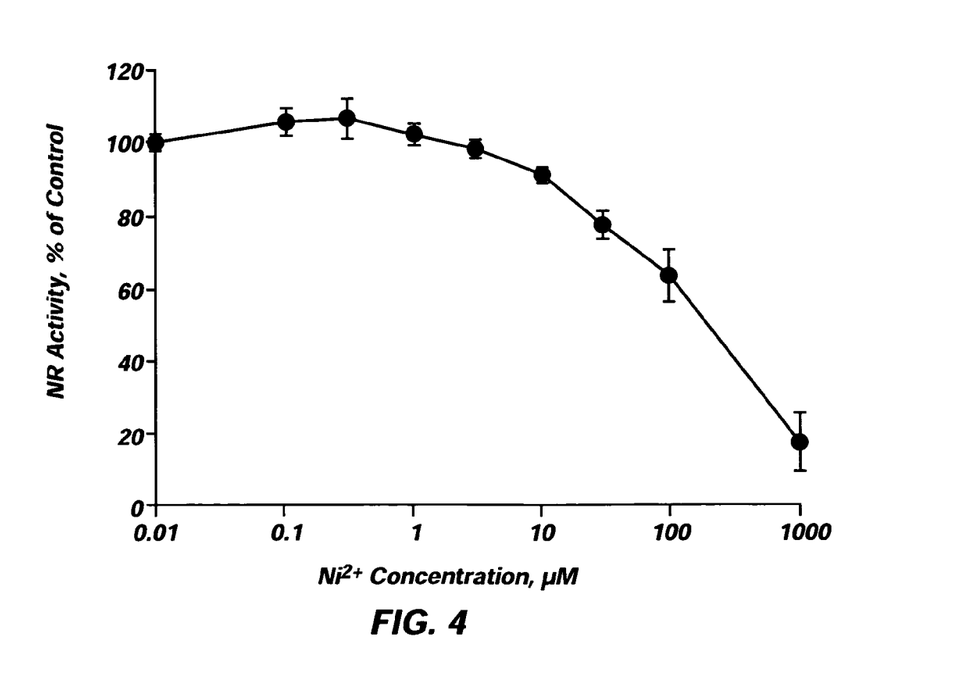
FIG. 4 is a graphic illustration of NR activity with increasing $Ni^{2+}$ concentrations.

As seen in FIG. 3, NR activity was inhibited over a small range of $Pb^{2+}$ $Zn^{2+}$, and $Cd^{2+}$ metal ion concentrations. NR showed less sensitivity to $Ni^{2+}$ and was not adversely affected by this metal ion until a concentration of over 100 µM, as illustrated in FIG. 4. Even at 1000 µM $Ni^{2+}$, the enzyme still retained nearly 20% of its original activity. NR activity is reported as a percent of a metal free control.

Figure 5:
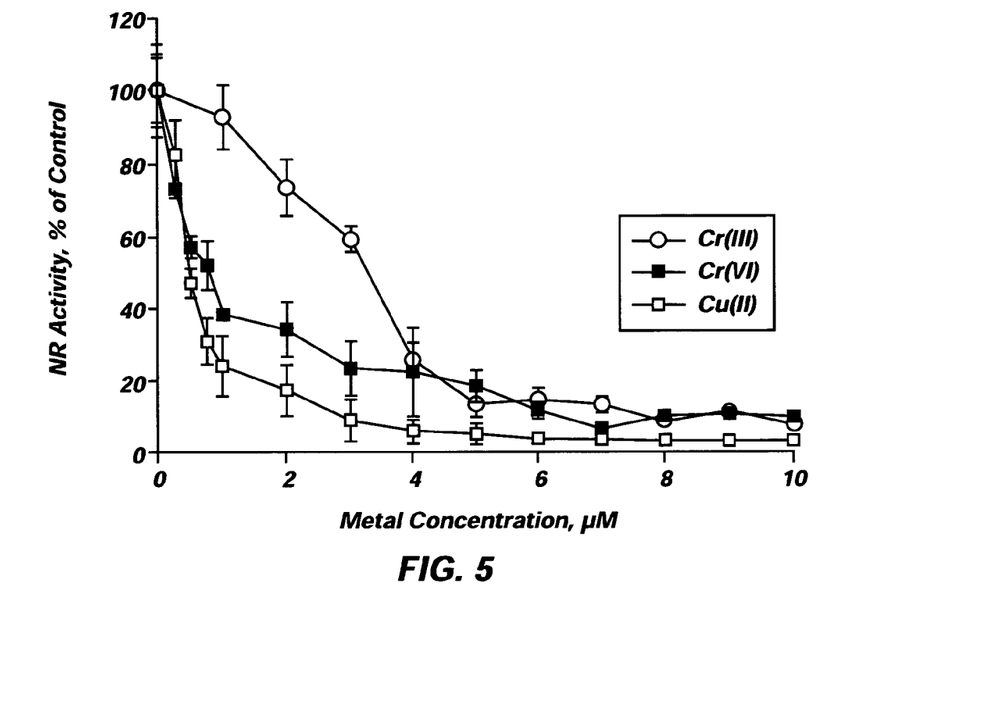
FIG. 5 is a graphic illustration of the greater impact of low concentrations of $Cu^{2+}$ and $Cr^{6+}$ when compared to $Cr^{3+}$ on NR activity.

Both $Cu^{2+}$ and $Cr^{6+}$ inhibited NR activity at concentrations below 1 µM with the enzyme inhibition of 76% and 62% at concentrations of 1 µM $Cu^{2+}$ and $Cr^{6+}$ respectively, as shown in FIG. 5. NR activity is reported as the percent of a metal-free control. However, $Cr^{3+}$ only substantially inhibited NR activity at a concentration above 4 µM. With the exception of $Cr^{6+}$ and $Cu^{2+}$, NR activity was not significantly affected by metal concentrations below 2 µM. Above 2 µM, NR activity decreased rapidly with increasing metal ion concentration and was almost completely inhibited by 10 µM concentrations of all metals tested other than $Ni^{2+}$. Nickel is much less inhibitory to NR activity than the metals in FIGS. 3 and 4.

In summary, the enzymatic activity of NR showed a sharp sensitivity to $Cr^{3+}$, $Cd^{2+}$, $Pb^{2+}$, and $Zn^{2+}$ over a range of 1–10 µM metal ion, while $Cu^{2+}$ and $Cr^{6+}$ inhibited the activity of NR across several orders of magnitude. $Cu^{2+}$ and $Cr^{6+}$ were the most potent inhibitors of NR and substantially inhibited activity at concentrations of 1 µM.

Example 4

EDTA and NTA Chelation Experiments

To determine the ability of chelating agents to prevent NR inhibition, EDTA or NTA was added to the enzymatic assay. For the experiments in which either EDTA or NTA was used, the reagents were added in the following order: the appropriate metal solution, EDTA or NTA, NR, nitrate, and finally NADPH. To allow sufficient time for the metal and chelating agent to react, the metal and either EDTA or NTA were added together prior to the addition of NR. Final assay metal ion concentrations ranged from 0.01 to 1000 µM. EDTA and NTA had final concentrations of 0.1 mM, 1 mM and 10 mM. Final concentrations of NR, $KNO_3$ and NADPH were as described above. NR activity was assayed by monitoring the production of nitrite, as described above.

Figure 6:
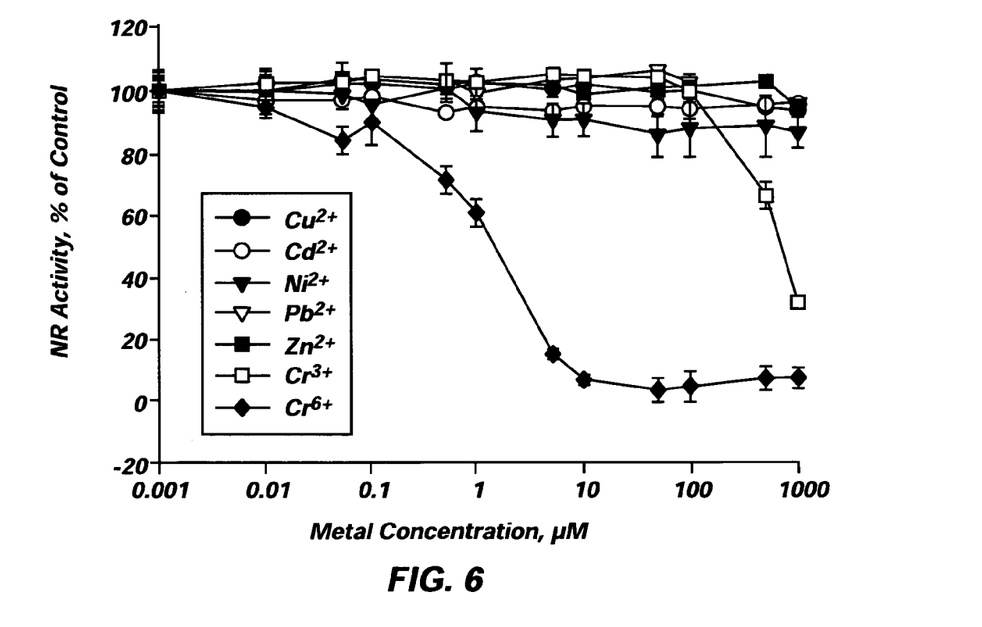
FIG. 6 is a graphic illustration showing the ability of 10 mM ethylenediaminetetraacetic acid ("EDTA") to protect NR activity from up to 100 mM of each metal, with the exception of $Cr^{6+}$.
Figure 7:
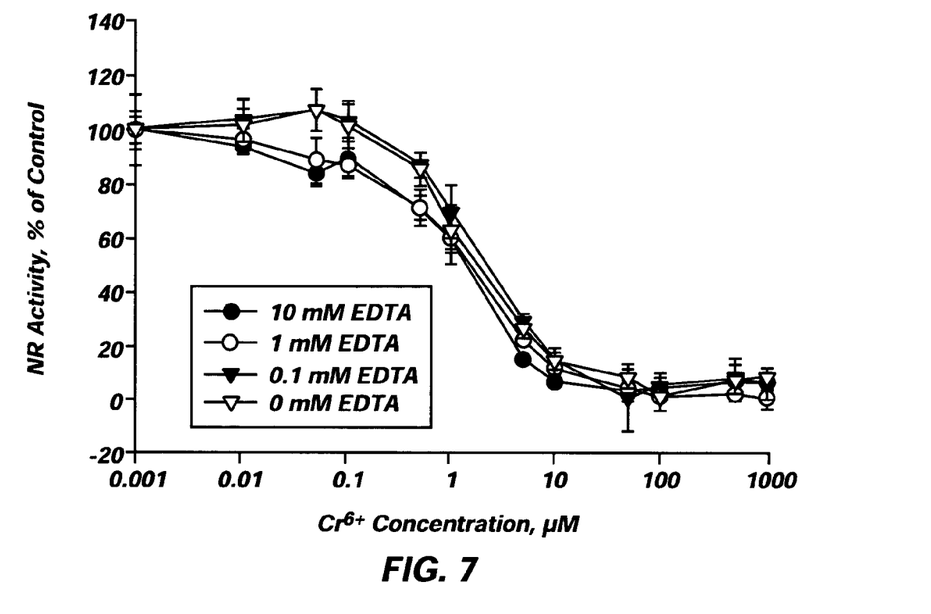
FIG. 7 is a graphic illustration showing that inhibition of NR activity by $Cr^{6+}$ is unchanged by the addition of increasing concentrations of EDTA to the assay.
Figure 8:
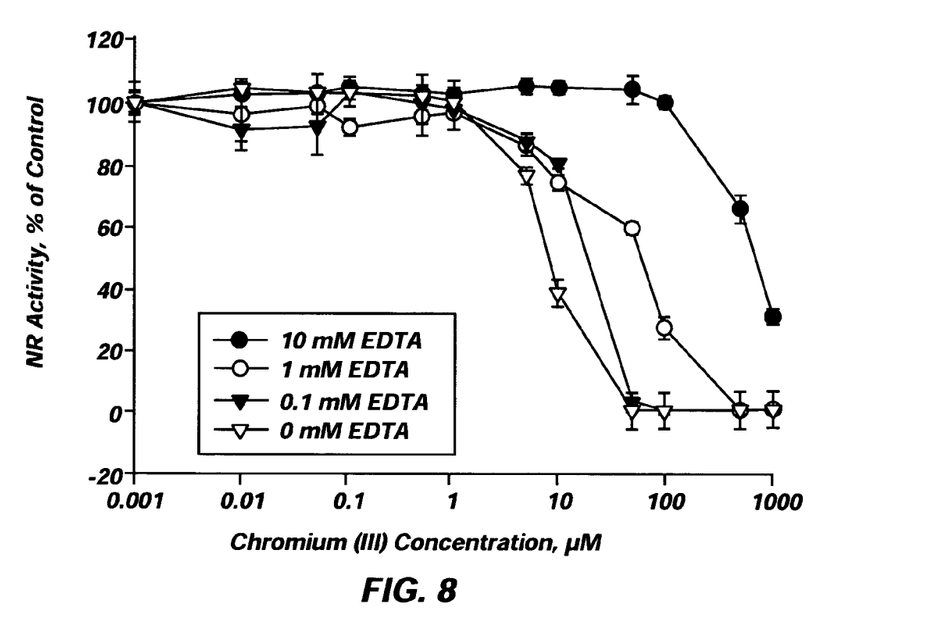
FIG. 8 is a graphic illustration showing that the addition of EDTA to the NR activity assays increases the concentration range over which NR is sensitive to $Cr^{3+}$ inhibition.

As shown in FIG. 6, 10 mM EDTA protected NR activity for all metal ions examined in this study up to metal concentrations of 100 μM, with the exception of $Cr^{6+}$. $Cr^{3+}$ was susceptible to chelation by 10 mM EDTA, and thus, was unavailable to inhibit NR at a concentration up to 100 μM $Cr^{3+}$. In contrast, the ability of $Cr^{6+}$ to inhibit NR was virtually unaffected by the presence of EDTA over the concentration range tested. The inhibition of NR activity by Cr(VI) is unchanged by the addition of increasing concentrations of EDTA, as shown in FIG. 7. As seen in FIG. 8, the addition of 10 mM EDTA increased the concentration range over which $Cr^{3+}$ inhibited NR by two orders of magnitude. By altering the concentrations of various chelating agents in the enzymatic assay, a wider range of metal concentrations may be quantified for a sample containing a single metal species as exemplified in FIG. 8 for $Cr^{3+}$ using EDTA and in FIG. 12 for $Cu^{2+}$ using NTA.

Figure 9:
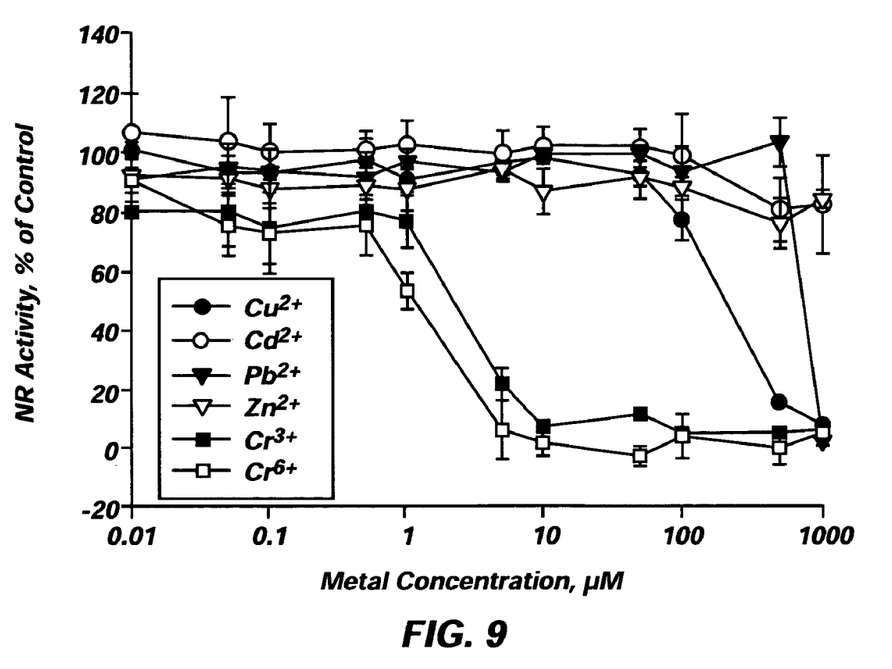
FIG. 9 is a graphic illustration showing that the addition of 10 mM nitrilotriacetic acid ("NTA") to the assay protected NR activity from metal inhibition from up to 100 mM of all metals with the exception of $Cr^{3+}$ and $Cr^{6+}$.
Figure 10:
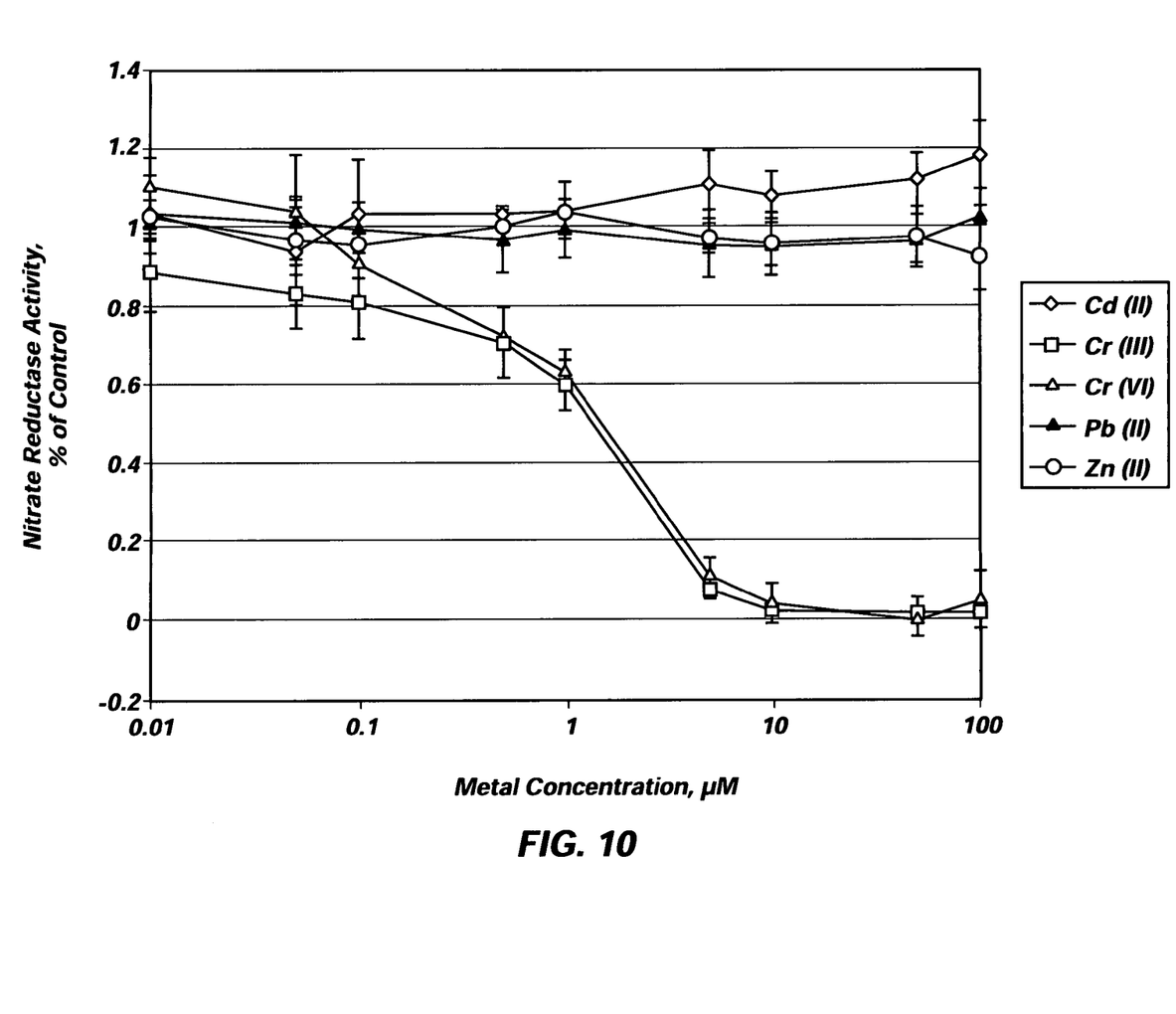
FIG. 10 is a graphic illustration showing that the addition of 1 mM NTA to the NR activity assays eliminates the inhibitory effects of the metals, except Cr(III) and Cr(VI)
Figure 11:
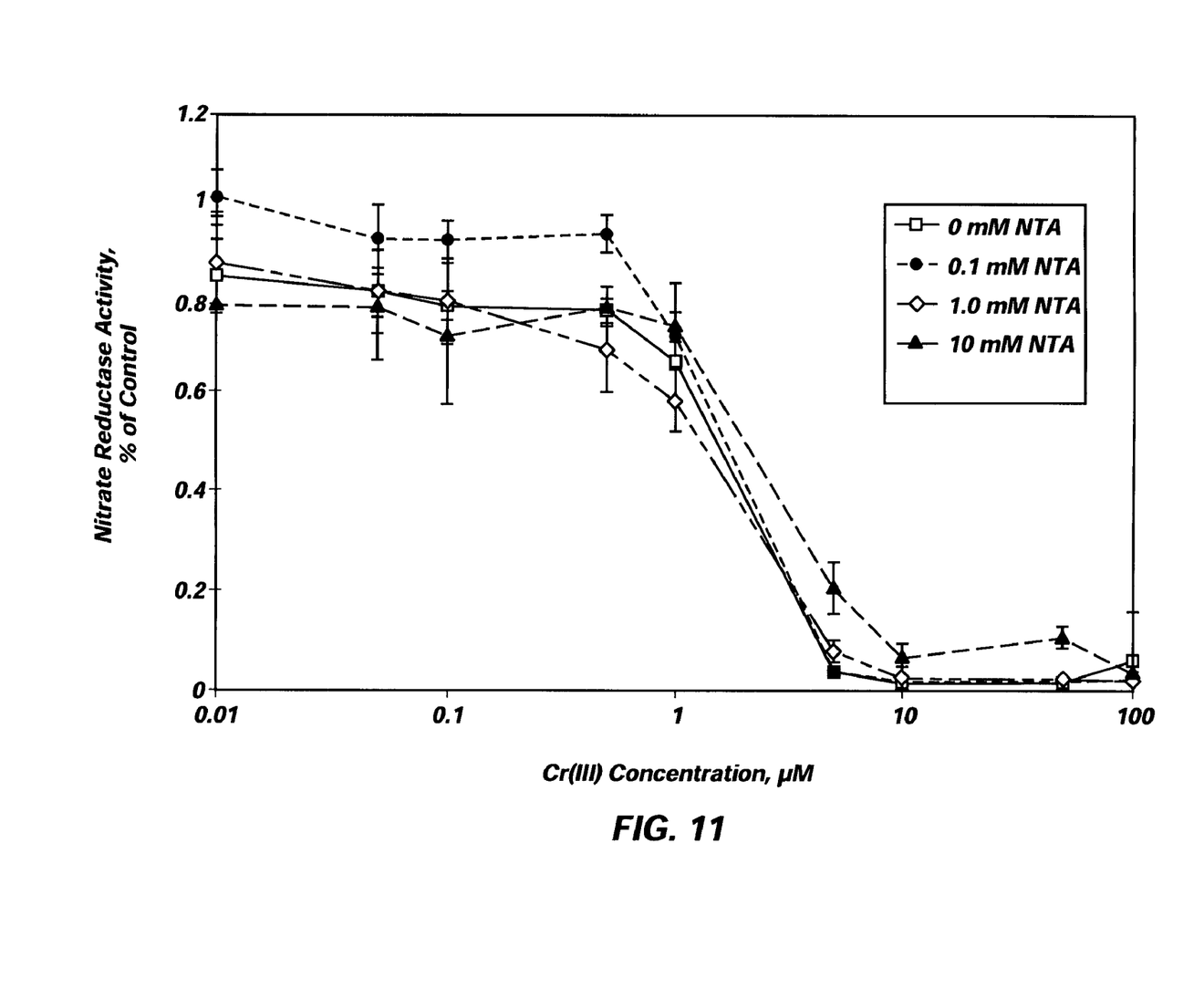
FIG. 11 is a graphic illustration showing that the addition of 10 mM NTA does not affect the inhibitory nature of Cr(III)
Figure 12:
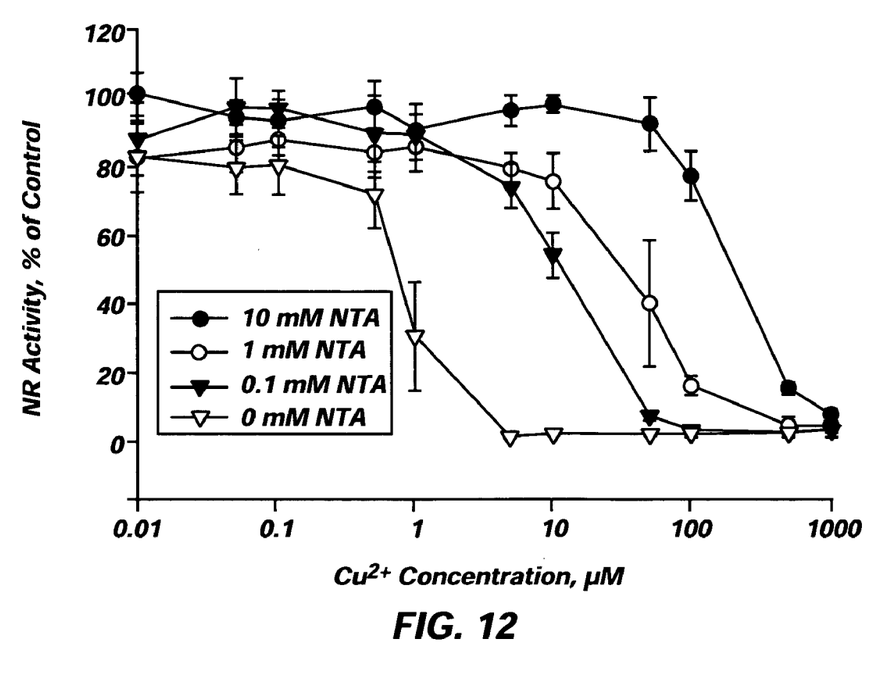
FIG. 12 is a graphic illustration showing that the addition of NTA to the NR activity assays increases the concentration range over which NR is sensitive to $Cu^{2+}$ inhibition.

FIG. 9 shows that 10 mM NTA protected NR from metal induced inhibition over metal concentrations of 0.01–1000 μM when added to the assay mixture concurrently with the metal stock solutions of $Zn^{2+}$, $Cu^{2+}$ up to 100 μM, $Pb^{2+}$ and $Cd^{2+}$, but did not protect NR from exposure to $Cr^{3+}$ or $Cr^{6+}$. FIG. 10 shows that a lower concentration of NTA, 1 mM NTA, also protected NR from metal induced inhibition over metal concentrations of 0.01–100 μM. However, the 1 mM NTA did not affect the inhibitory effects of $Cr^{3+}$ or $Cr^{6+}$. The inhibitory effects of Cr(III) on NR activity were not affected up to 10 mM NTA, which is shown in FIG. 11. FIG. 12 shows that the addition of NTA to the NR activity assays increased the concentration range over which NR is sensitive to $Cu^{2+}$, inhibition.

Since EDTA chelated all of the tested metals except $Cr^{6+}$, NR was only inhibited by $Cr^{6+}$ in the presence of EDTA. In contrast, NR was only inhibited by $Cr^{3+}$ and $Cr^{6+}$ in the presence of NTA. This difference in chelation between EDTA and NTA is used to quantify total Cr present in the sample and to differentiate between the $Cr^{3+}$ and $Cr^{6+}$ species of Cr. This method bypasses the need for expensive testing by ICP-MS and provides a rapid, cost effective means of quantifying $Cr^{3+}$ ions in solution.

Example 5

Regeneration of NR Activity

To determine whether inhibition caused by exposure to the metals could be reversed by the addition of EDTA, NR was exposed to 100 μM of the following metals: $Cd^{2+}$, $Cr^{3+}$, $Cu^{2+}$, $Pb^{2+}$ and $Zn^{2+}$ for five minutes in a 96-well plate and incubated at 25° C. with 10 mM $KNO_3$. After five minutes, 10 mM EDTA was added and solutions were shaken for 10 seconds. NADPH was added to sets of positive controls, negative controls, and metal/NR and EDTA for evaluation of NR activity both immediately after EDTA addition and 30 minutes after EDTA addition. Enzyme activity was measured by determining the amount of nitrite produced and reported as a percent of a positive control. As shown in Table 1, the EDTA partially restored activity to NR that was exposed to $Zn^{2+}$, $Pb^{2+}$, and $Cd^{2+}$ but was unable to significantly restore NR activity when exposed to either $Cu^{2+}$ or $Cr^{3+}$. The recovery of NR activity after exposure to $Cr^{6+}$ ions via EDTA chelation was not tested since previous experiments showed that EDTA was not able to protect NR from $Cr^{6+}$ inhibition.

TABLE 1

Recover of metal inactivated nitrate reductase activity by 10 mM EDTA

| Metal Ion | $Zn^{2+}$ % of control | $Pb^{2+}$ % of control | $Cd^{2+}$ % of control | $Cr^{3+}$ % of control | $Cu^{2+}$ % of control |
|---|---|---|---|---|---|
| NR activity before EDTA treatment | 6.6% ± 2.8% | 1.3% ± 0.4% | 2.7% ± 2.6% | 5.7% ± 10% | 1.0% ± 0.3% |
| NR activity after EDTA treatment | 54% ± 4.0% | 40% ± 5.4% | 28% ± 1.9% | 4.3% ± 1.9% | 5.1% ± 1.5% |

The present invention includes detecting and quantifying at least one metal of interest in a sample. The method comprises using an enzymatic assay to detect and quantify the metal of interest. In addition, a method of speciating between multiple valence states of the metal of interest by using the enzymatic assay is also encompassed by the present invention, as is a biosensor that utilizes the enzymatic assay.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An apparatus for detecting a presence or absence of a metal of interest in a sample containing a plurality of metals comprising:
    a biosensor comprising an electron carrier immobilized to a surface of an electrode and a layer of an immobilized enzyme adjacent to the electrode, wherein the immobilized enzyme comprises an enzyme inhibited by the metal of interest; and
    at least one chelating agent selected to chelate a portion of the plurality of metals without chelating the metal of interest.

2. The apparatus of claim 1, wherein the electron carrier is nicotinamide adenine dinucleotide or nicotinamide adenine dinucleotide phosphate.

3. The apparatus of claim 2, wherein the immobilized enzyme is nitrate reductase.

4. The apparatus of claim 3, wherein the nitrate reductase is crosslinked to the layer of the immobilized enzyme.

5. The apparatus of claim 2, wherein the immobilized enzyme is inhibited by the presence of chromium in the sample.

6. The apparatus of claim 1, wherein the electrode is a gold electrode.

7. The apparatus of claim 1, wherein the metal of interest is chromium.

8. The apparatus of claim 1, where in the plurality of metals is selected from the group consisting of chromium, copper, lead, cadmium, nickel, zinc, arsenic, mercury, silver, and mixtures thereof.

9. An apparatus for detecting a presence or absence of a valence state of interest of a metal of interest in a sample containing a plurality of metals comprising:
    a biosensor comprising an electron carrier immobilized to a surface of an electrode and a layer of an immobilized enzyme adjacent to the electrode, wherein the immobilized enzyme comprises an enzyme inhibited by the valence state of interest of the metal of interest; and at least one chelating agent selected to chelate a portion of the plurality of metals without chelating the valence state of interest of the metal of interest.

10. The apparatus of claim 9, wherein the electron carrier is nicotinamide adenine dinucleotide or nicotinamide adenine dinucleotide phosphate.

11. The apparatus of claim 10, wherein the immobilized enzyme is inhibited by the presence of chromium in the sample.

12. The apparatus of claim 9, wherein the electrode is a gold electrode.

13. The apparatus of claim 12, wherein the immobilized enzyme is nitrate reductase.

14. The apparatus of claim 13, wherein the nitrate reductase is crosslinked to the layer of the immobilized enzyme.

15. The apparatus of claim 9, wherein the valence state of interest of the metal of interest is a chromium ion.

16. The apparatus of claim 9, where in the plurality of metals is selected from the group consisting of chromium, copper, lead, cadmium, nickel, zinc, arsenic, mercury, silver, and mixtures thereof.

17. An apparatus for detecting a presence or absence of a valence state of interest of chromium in a sample containing a plurality of metals in one or more valence states comprising:

a biosensor comprising an electron carrier immobilized to a surface of an electrode and a layer of an immobilized enzyme adjacent to the electrode, wherein the immobilized enzyme comprises an enzyme inhibited by the valence state of interest of chromium; and at least one chelating agent selected to chelate a portion of the plurality of metals without chelating the valence state of interest of chromium.

18. The apparatus of claim 17, wherein the electron carrier is nicotinamide adenine dinucleotide or nicotinamide adenine dinucleotide phosphate.

19. The apparatus of claim 17, wherein the electrode is a gold electrode.

20. The apparatus of claim 19, wherein the immobilized enzyme is nitrate reductase.

* * * * *